US012663536B2

(12) United States Patent
Khasnobish et al.

(10) Patent No.: US 12,663,536 B2
(45) Date of Patent: Jun. 23, 2026

(54) METHOD AND SYSTEM FOR MILLIMETER WAVE SYNTHETIC APERTURE RADAR IMAGING FOR SUPERFICIAL IMPLANT MONITORING

(71) Applicant: Tata Consultancy Services Limited, Mumbai (IN)

(72) Inventors: Anwesha Khasnobish, Kolkata (IN); Chirabrata Bhaumik, Kolkata (IN); Tapas Chakravarty, Kolkata (IN); Smriti Rani, Bangalore (IN); Amit Swain, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 279 days.

(21) Appl. No.: 18/659,122

(22) Filed: May 9, 2024

(65) Prior Publication Data

US 2024/0385314 A1 Nov. 21, 2024

(30) Foreign Application Priority Data

May 17, 2023 (IN) .............................. 202321034661

(51) Int. Cl.
*G01S 13/90* (2006.01)
*A61B 5/0507* (2021.01)
*G01S 7/288* (2006.01)

(52) U.S. Cl.
CPC ........ *G01S 13/9019* (2019.05); *A61B 5/0507* (2013.01); *G01S 7/2883* (2021.05); *G01S 13/9017* (2013.01)

(58) Field of Classification Search
CPC ... A61B 2576/00; A61B 5/0507; A61B 5/061; A61B 5/4887; A61B 5/7257;
(Continued)

(56) References Cited

U.S. PATENT DOCUMENTS 6,061,589 A * 5/2000 Bridges ................ A61B 6/0435
600/430
6,263,230 B1 * 7/2001 Haynor .................. A61B 34/20
600/424
(Continued)

FOREIGN PATENT DOCUMENTS

EP 2284569 A1 2/2011
IN 202221057044 4/2024
WO WO2022260935 A1 12/2022

*Primary Examiner* — Peter M Bythrow
(74) *Attorney, Agent, or Firm* — Finnegan, Henderson, Farabow, Garrett & Dunner, LLP

(57) ABSTRACT

Millimeter (mm) waves, in comparison to microwaves, have short wavelengths and can penetrate to few centimeters inside the body. The embodiments herein provide a method and system for millimeter (mm) wave synthetic aperture radar (SAR) imaging for superficial implant monitoring. The mmWave SAR and consecutive an autofocusing SAR imaging are suitable for a superficial tissue and subsequent continuous implant monitoring due to their smaller form-factor and faster processing coupled with focused dielectric lens. Additionally, a limb topography is approximated for localization of implant region on interest (ROI) in the SAR amplitude image. Further, the method and system provide a bone implant monitoring in order to assess any unwanted mobility or dislocation of the implant, and thus bone health is a critical issue.

12 Claims, 6 Drawing Sheets

(58) Field of Classification Search
CPC ............. G01S 13/9011; G01S 13/9017; G01S
13/9019; G01S 13/9054; G01S 7/2883;
G01S 13/88; G01S 13/887
See application file for complete search history.

(56) References Cited

U.S. PATENT DOCUMENTS

| | | | |
|---|---|---|---|
| 7,671,784 B2 * | 3/2010 | Steinway ................. | A61B 5/05 |
| | | | 600/407 |
| 7,769,422 B2 * | 8/2010 | DiSilvestro .......... | A61B 5/6828 |
| | | | 600/595 |
| 11,278,241 B2 * | 3/2022 | Baheti .................... | A61B 5/681 |
| 12,360,234 B1 * | 7/2025 | Short, Jr. ............. | G01N 37/005 |
| 2005/0062639 A1 * | 3/2005 | Biggs ...................... | G01S 13/89 |
| | | | 342/194 |
| 2005/0099290 A1 * | 5/2005 | Govari ................... | A61B 5/062 |
| | | | 340/8.1 |
| 2006/0170584 A1 * | 8/2006 | Romero ............... | A61B 5/0507 |
| | | | 342/179 |
| 2007/0060816 A1 * | 3/2007 | Simpkin .............. | A61B 5/0507 |
| | | | 600/430 |
| 2007/0293752 A1 * | 12/2007 | Simpkin ................ | A61B 5/442 |
| | | | 600/407 |
| 2009/0192384 A1 * | 7/2009 | Fontius .................. | A61B 5/704 |
| | | | 600/425 |
| 2009/0309786 A1 * | 12/2009 | Stolpman ............. | A61B 5/0507 |
| | | | 342/25 A |
| 2010/0274122 A1 * | 10/2010 | DiSilvestro ............ | A61B 5/702 |
| | | | 600/424 |
| 2013/0082870 A1 * | 4/2013 | Chambers ............. | G01S 13/003 |
| | | | 342/25 A |
| 2013/0225988 A1 * | 8/2013 | Mahfouz .............. | A61B 5/0507 |
| | | | 600/430 |
| 2014/0226850 A1 * | 8/2014 | Beer ........................ | G01V 3/12 |
| | | | 382/103 |
| 2016/0120407 A1 * | 5/2016 | Martinez-Lorenzo ....................... | |
| | | | A61B 6/025 |
| | | | 600/427 |
| 2020/0132832 A1 * | 4/2020 | Alalusi ................. | G01S 13/886 |
| 2020/0397336 A1 * | 12/2020 | Sherry ................... | H04N 23/56 |
| 2021/0137406 A1 * | 5/2021 | Lepple-Wienhues ......................... | |
| | | | A61B 5/0507 |
| 2022/0287582 A1 * | 9/2022 | Cano Garcia ........ | A61B 5/0507 |
| 2022/0397660 A1 * | 12/2022 | Mirbeik-Sabzevari ...................... | |
| | | | A61B 5/05 |

* cited by examiner

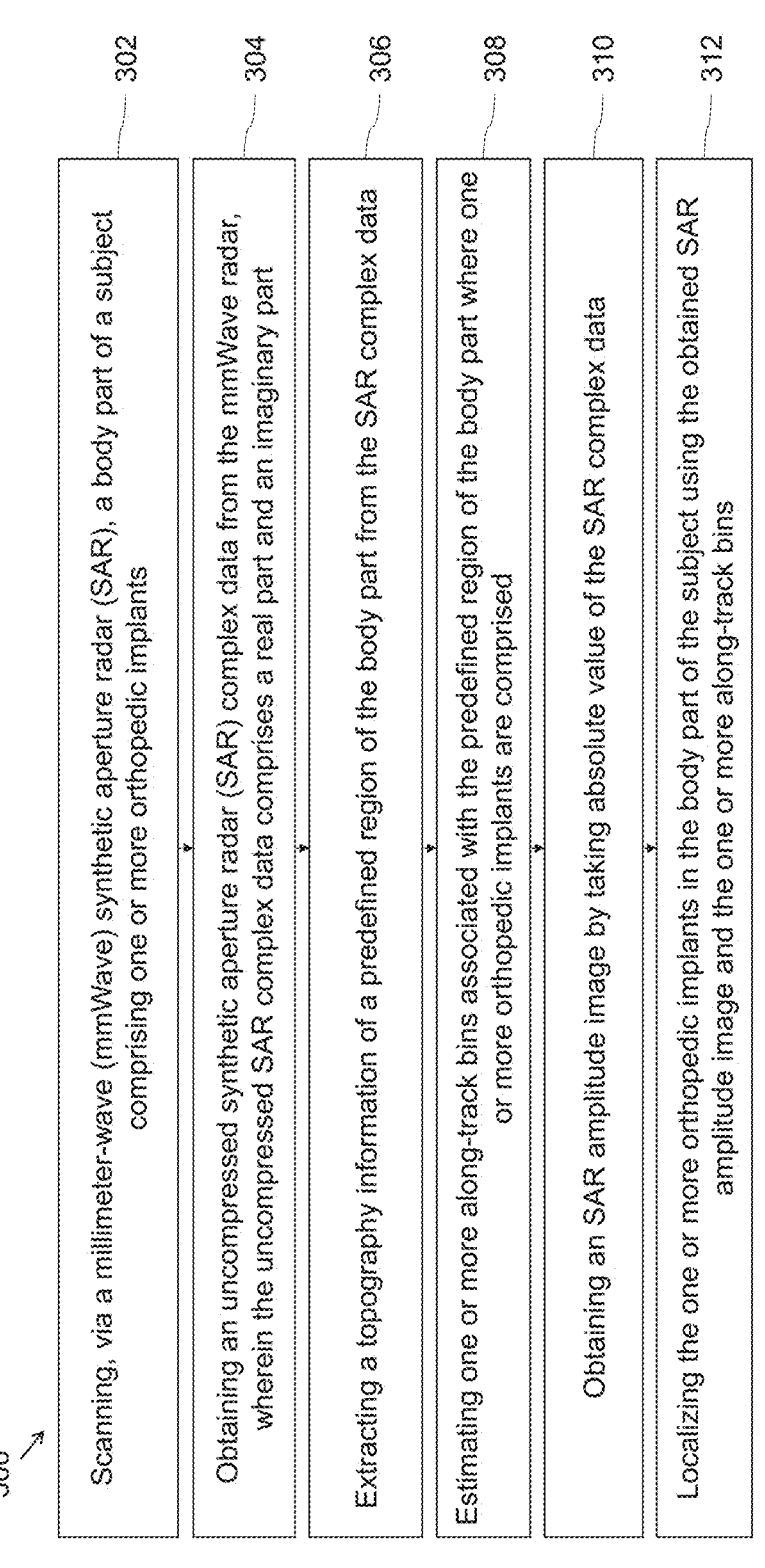

300

302 — Scanning, via a millimeter-wave (mmWave) synthetic aperture radar (SAR), a body part of a subject comprising one or more orthopedic implants 304 — Obtaining an uncompressed synthetic aperture radar (SAR) complex data from the mmWave radar, wherein the uncompressed SAR complex data comprises a real part and an imaginary part 306 — Extracting a topography information of a predefined region of the body part from the SAR complex data 308 — Estimating one or more along-track bins associated with the predefined region of the body part where one or more orthopedic implants are comprised 310 — Obtaining an SAR amplitude image by taking absolute value of the SAR complex data 312 — Localizing the one or more orthopedic implants in the body part of the subject using the obtained SAR amplitude image and the one or more along-track bins

FIG. 3

METHOD AND SYSTEM FOR MILLIMETER WAVE SYNTHETIC APERTURE RADAR IMAGING FOR SUPERFICIAL IMPLANT MONITORING

PRIORITY CLAIM

This U.S. patent application claims priority under 35 U.S.C. § 119 to Indian application Ser. No. 20/232,1034661, filed on May 17, 2023. The entire content of the abovementioned application is incorporated herein by reference.

Technical Field

The disclosure herein generally relates to the field of implant monitoring and more specifically, to a method and system for millimeter wave Synthetic Aperture Radar (SAR) imaging for superficial implant monitoring.

Background

Orthopedic implant mobility monitoring is essential for assessing bone and implant condition post-surgery. This information can be used to evaluate the success of the surgery and make necessary adjustments to the implant to ensure optimal function and patient outcomes. Implant mobility monitoring can also help detect any potential complications or issues with the implant, such as wear or loosening, which can then be addressed before they cause significant harm due to skin impingement.

The gold standard for localization of orthopedic implants are X-rays, CT scans and MRI for the medical community worldwide. Although useful and reliable, the bulky machinery involved are not portable, cannot be used continuously and repeatedly and also cannot be performed outside hospital emergency rooms. For cases where patient agility is difficult due to patient condition, logistics and need for continuous and quick monitoring serves a bottleneck.

Existing systems and methods are using sensors embedded within the implants for implant monitoring. However, for orthopedic implants this type of implant load monitoring is capable of giving information about the osteo-integration, implant condition, but implant mobility in terms of localization is not achieved.

SUMMARY

Embodiments of the disclosure present technological improvements as solutions to one or more of the above-mentioned technical problems recognized by the inventors in conventional systems. For example, in one embodiment, a method and system for millimeter wave synthetic aperture radar (SAR) imaging for superficial implant monitoring is provided.

In one aspect, a processor-implemented method for millimeter wave Synthetic Aperture Radar (SAR) imaging for superficial implant monitoring is provided. The processor-implemented method includes one or more steps such as scanning, via a millimeter-wave (mmWave) Synthetic Aperture Radar (SAR), a body part of a subject comprising one or more orthopedic implants and obtaining an uncompressed Synthetic Aperture Radar (SAR) complex data from the mmWave radar, wherein the uncompressed SAR complex data comprises a real part and an imaginary part. Further, the processor-implemented method comprising estimating one or more along-track bins associated with the predefined region of the body part where one or more orthopedic implants are comprised, wherein the one or more along-track bins provide a predefined location of the topography information of the body part in a SAR image. Furthermore, the processor-implemented method comprising obtaining an SAR amplitude image by taking absolute value of the SAR complex data and localizing the one or more orthopedic implants in the body part of the subject using the obtained SAR amplitude image and the one or more along-track bins.

In another aspect, a system for millimeter wave synthetic aperture radar (SAR) imaging for superficial implant monitoring is provided. The system includes an input/output interface configured to scan a body part of a subject comprising one or more orthopedic implants using a millimeter-wave (mmWave) Synthetic Aperture Radar (SAR), one or more hardware processors and at least one memory storing a plurality of instructions, wherein the one or more hardware processors are configured to execute the plurality of instructions stored in the at least one memory.

Further, the system is configured to obtain an uncompressed Synthetic Aperture Radar (SAR) complex data from the mmWave radar, wherein the uncompressed SAR complex data comprises a real part and an imaginary part. Furthermore, the system is configured to obtain an uncompressed Synthetic Aperture Radar (SAR) complex data from the mmWave radar, wherein the uncompressed SAR complex data comprises a real part and an imaginary part. Further, the system is configured to extract a topography information of a predefined region of the body part from the SAR complex data. Furthermore, the system is configured to estimate one or more along-track bins associated with the predefined region of the body part where one or more orthopedic implants are comprised, wherein the one or more along-track bins provide a predefined location of the topography information of the body part in a SAR image. Finally, the system is configured to obtain an SAR amplitude image by taking absolute value of the SAR complex data and localize the one or more orthopedic implants in the body part of the subject using the obtained SAR amplitude image and the one or more along-track bins.

In yet another aspect, one or more non-transitory machine-readable information storage mediums are provided comprising one or more instructions, which when executed by one or more hardware processors causes a method for millimeter wave Synthetic Aperture Radar (SAR) imaging for superficial implant monitoring is provided. The processor-implemented method includes one or more steps such as scanning, via a millimeter-wave (mmWave) synthetic aperture radar (SAR), a body part of a subject comprising one or more orthopedic implants and obtaining an uncompressed Synthetic Aperture Radar (SAR) complex data from the mmWave radar, wherein the uncompressed SAR complex data comprises a real part and an imaginary part. Further, the processor-implemented method comprising estimating one or more along-track bins associated with the predefined region of the body part where one or more orthopedic implants are comprised, wherein the one or more along-track bins provide a predefined location of the topography information of the body part in a SAR image. Furthermore, the processor-implemented method comprising obtaining an SAR amplitude image by taking absolute value of the SAR complex data and localizing the one or more orthopedic implants in the body part of the subject using the obtained SAR amplitude image and the one or more along-track bins.

It is to be understood that the foregoing general descriptions and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3 is a flowchart of a method for millimeter wave Synthetic Aperture Radar (SAR) imaging for superficial implant monitoring using FIG. 2, in accordance with some embodiments of the present disclosure.

DETAILED DESCRIPTION

Figure 1:
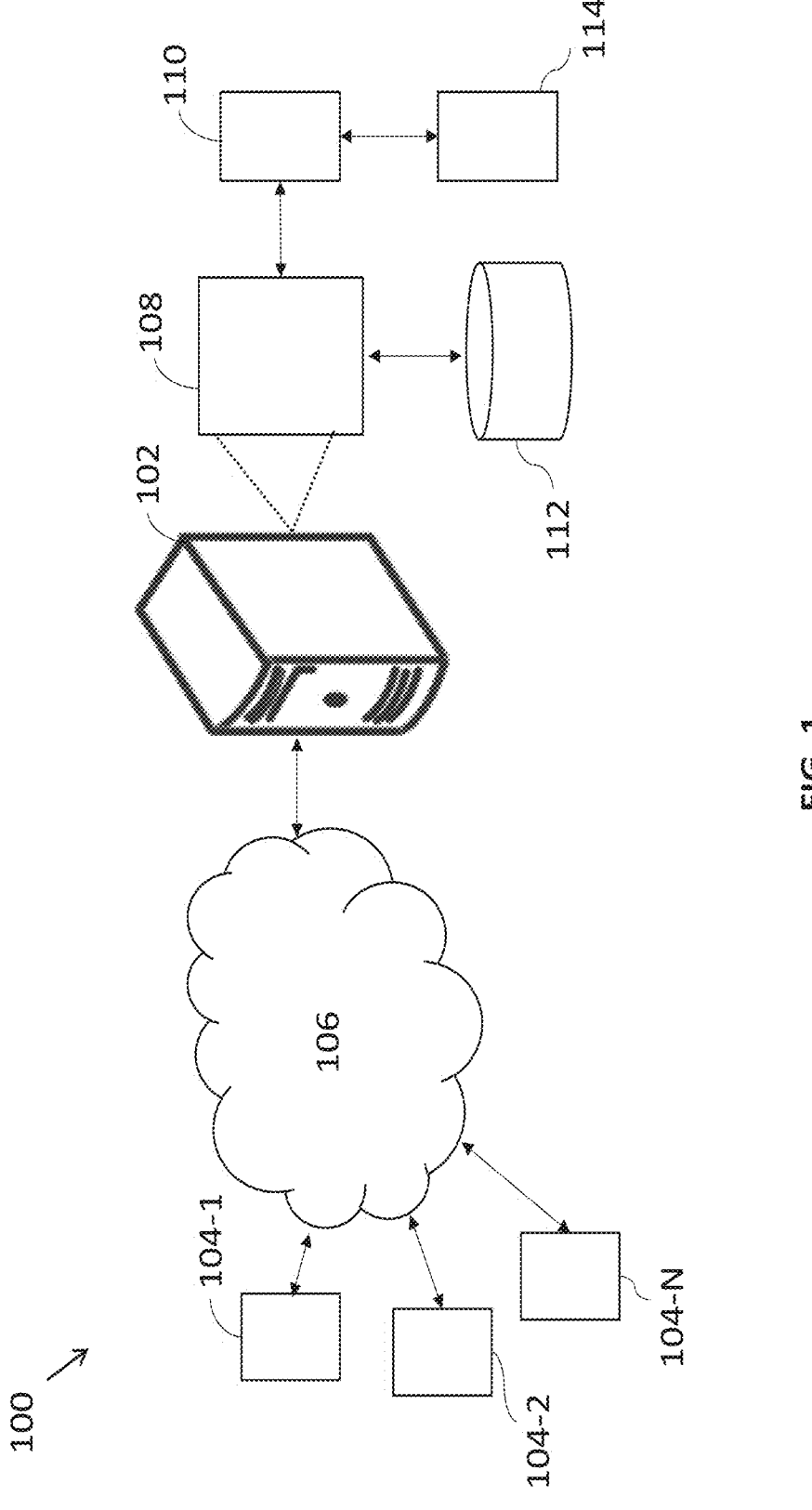
FIG. 1 illustrates a block diagram of an exemplary system for millimeter wave Synthetic Aperture Radar (SAR) imaging for superficial implant monitoring, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Millimeter (mm) waves, in comparison to microwaves, have short wavelengths and can penetrate to few centimeters inside the body. Thus, the mmWave imaging of implant is possible in areas of the body where the implants are seated just beneath skin at sub-centimeter depths. In case of distal tibial fractures, the interlocking screws are closely co-located and are in close proximity to the epidermis. Additionally, the subcutaneous soft tissues of the distal tibia are thin. Subsequently, making this an excellent candidate for the mmWave imaging of metallic implants with good contrast due to their strong reflectivity as compared to the background.

The mmWave imaging allows for smaller antennae, making it feasible for portable and at home/at clinic monitoring. Additionally, di-electric lenses coupled with millimeter wave radars enable higher gain and enhanced focusing of the beam to a relatively smaller region. They also provide resolution in mm range, thus proving to be a good alternative for being a portable alternative mmWave imaging for implant monitoring.

Typically, for the comfort or ease of patients and clinicians, the off-body imaging apparatus is preferred to be mobile and not vice versa. Synthetic Aperture Radar (SAR) is a radar imaging paradigm that provides an azimuth resolution superior to that achievable using the radar's real aperture. Due to the movement of radar antenna, this long synthetic aperture is generated pertaining to the radar platform's trajectory. Utilizing this, various SAR image formation algorithms have been designed and implemented. Further, a Range Doppler Algorithm (RDA) has been employed to identify and resolute implants. The RDA is a well-known method for processing and generating images using strip map mode SAR. It leverages the simplicity of independent and one-dimensional frequency domain operations along the range and azimuth dimension. It compresses the raw SAR data using matched filters in both these dimensions.

The embodiments herein provide a method and system for millimeter wave Synthetic Aperture Radar (SAR) imaging for superficial implant monitoring, in accordance with some embodiments of the present disclosure. The method and system provide a bone implant monitoring in order to assess any unwanted mobility or dislocation of the implant, and thus bone health is a critical issue. The disclosed approach is safe, portable, does not use ionizing rays, portable, and can be continuously or repeatedly used even outside emergency rooms. Herein, a 60 GHz pulse coherent radar is used on a moving platform to scan an object of interest. Further herein, an auto-focusing technique helps to generate SAR images for the inhomogeneous human body/phantoms. It would be appreciated that the method detects superficial screw implants on sawbones phantom and human tibial screws with an accuracy of 100% and 76.2% respectively.

Referring now to the drawings, and more particularly to FIG. 1 through FIG. 4, where similar reference characters denote corresponding features consistently throughout the figures, there are shown preferred embodiments, and these embodiments are described in the context of the following exemplary system and/or method.

FIG. 1 illustrates a block diagram of a system 100 for a millimeter (mm) wave Synthetic Aperture Radar (SAR) imaging for a superficial implant monitoring, in accordance with an example embodiment. Although the present disclosure is explained considering that the system 100 is implemented on a server, it may be understood that the system 100 may comprise one or more computing devices 102, such as a laptop computer, a desktop computer, a notebook, a workstation, a cloud-based computing environment and the like. It will be understood that the system 100 may be accessed through one or more input/output interfaces 104-1, 104-2 . . . 104-N, collectively referred to as I/O interface 104. Examples of the I/O interface 104 may include, but are not limited to, a user interface, a portable computer, a personal digital assistant, a handheld device, a smartphone, a tablet computer, a workstation, and the like. The I/O interface 104 is communicatively coupled to the system 100 through a network 106.

In an embodiment, the network 106 may be a wireless or a wired network, or a combination thereof. In an example, the network 106 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 106 may include a variety of network devices, including routers, bridges, servers, computing devices, storage devices. The network devices within the network 106 may interact with the system 100 through communication links.

The system 100 supports various connectivity options such as BLUETOOTH®, USB, ZigBee, and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. Further, the system 100 comprises at least one memory 110 with a plurality of instructions, one or more databases 112, and one or more hardware processors 108 which are communicatively coupled with the at least one memory 110 to execute a plurality of modules 114 therein. The components and functionalities of the system 100 are described further in detail.

Figure 2:
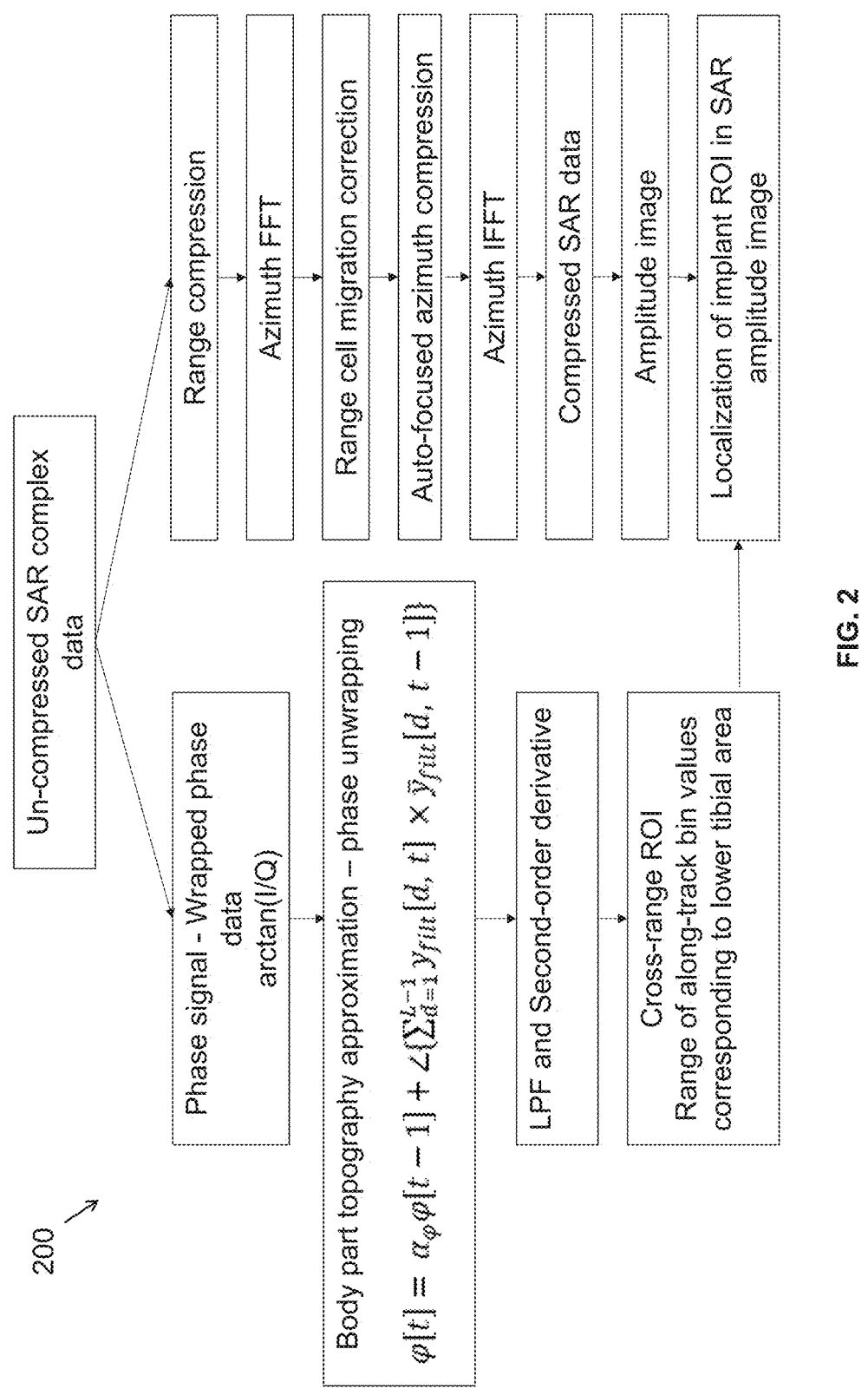
FIG. 2 is a functional block diagram of the system for millimeter wave Synthetic Aperture Radar (SAR) imaging for superficial implant monitoring using FIG. 1, in accordance with some embodiments of the present disclosure.

FIG. 2 is a functional block diagram of the system 100 for millimeter wave Synthetic Aperture Radar (SAR) imaging for superficial implant monitoring implemented by the system 100 of FIG. 1. Herein, uncompressed SAR complex data is received from the radar, which is basically the radar backscattered signal.

FIG. 3 is an exemplary flow diagram illustrating a processor-implemented method 300 for millimeter (mm) wave Synthetic Aperture Radar (SAR) imaging for superficial implant monitoring implemented by the system 100 of FIG. 1. Functions of the components of the system 100 are now explained through steps of flow diagram in FIG. 2, according to some embodiments of the present disclosure.

Initially, at step 302 of the processor-implemented method 300, the one or more hardware processors 108 are configured by the programmed instructions to scan a body part of a subject comprising one or more orthopedic implants via a millimeter-wave (mmWave) SAR.

At the next step 304 of the method 300, the one or more hardware processors 108 are configured by the programmed instructions to obtain an uncompressed Synthetic Aperture Radar (SAR) complex data from the mmWave SAR. The uncompressed SAR complex data comprises a real part and an imaginary part of the SAR.

In one embodiment, wherein the SAR amplitude image is obtained by performing a range compression on the SAR complex data to obtain a range-compressed matrix. The range compression carries out a fast-time convolution. This refers to performing a Fast Fourier Transform (FFT) on the matrix along the range direction. Then, a matched filter operation is carried out with the range reference function followed by range an Inverse Fast Fourier Transform (IFFT) to infer matrix.

Further, an azimuth FFT is performed on the range-compressed matrix to obtain a range doppler matrix. Furthermore, an azimuth compression is performed by multiplying the range doppler matrix with FFT of a time-domain azimuth reference function to get the matched filter output and an azimuth IFFT is performed to transform matched filter output into a time domain to form a complex image matrix. Due to the motion of the radar platform with respect to the object, the range profile of an object shifts to multiple range bins. A Range Cell Migration Correction (RCMC) re-arranges the data based on the object shifting and mitigates the introduced phase errors to straighten the trajectory. Further, the range cell migration correction comprises of two components namely range walk and range curvature. The range walk causes a shift of range bins along the fast-time dimension. Over a coherent processing interval of duration T, the magnitude of the range-walk ($R_\omega$) is:

$$\Delta R_\omega = VT\sin\theta \qquad (1)$$

wherein V is the platform velocity and $\theta$ is the squint angle. The range curvature ($R_c$) results in migration of data from a given scatterer to another range bin in a curved fashion. This deviation is given by a quadratic expression—

$$\Delta R_c = (VT\cos\theta)^2/8R_0 \qquad (2)$$

wherein $R_0$ is the range around which correction is done.

In another aspect, the azimuth compression confines the energy in the trajectory to a single cell in the azimuth direction. A matched filter is applied to the data based on the azimuth reference function. It consists of a linear term whose coefficient i.e., the Doppler centroid ($f_{dc}$) is given by $$f_{dc} = -\frac{2V}{\lambda}\sin(\theta),$$

and the co-efficient of the quadratic term known as the doppler frequency rate ($f_r$) denoted by $$f_r = -\frac{2V^2}{\lambda R_0}\cos^2\theta.$$

The resulting azimuth reference function is as follows:

$$\theta(t) = e^{i\left(\frac{4\pi R_0}{\lambda}\right)}.e^{i2\pi\left[f_{dc}(t)+f_r\left(\frac{t^2}{2}\right)\right]} \qquad (3)$$

wherein $\theta(t)$ is the time domain phase reference function, $\lambda$ is the transmitting wavelength, and $R_0$ is the target range. The range-doppler matrix (D) is multiplied with the Fast Fourier Transform (FFT) of the time-domain azimuth reference function. Lastly, an azimuth Inverse Fast Fourier Transform (IFFT) is performed to transform the data into the time domain. This gives us the final compressed SAR image.

At the next step 306 of the method 300, the one or more hardware processors 108 are configured by the programmed instructions to extract a topography information of a pre-defined region of the body part from the SAR complex data. Herein, in-phase and quadrature phase components of the SAR complex data are obtained. An arctan operation is performed on the SAR complex data to obtain a phase of the SAR complex data. The phase of SAR complex data is unwrapped by using the expression and applying a low pass filter on the unwrapped phase of the SAR complex data to obtain a low pass filtered unwrapped phase using the following expression to approximate the topography of the body part.

$$\varphi[t] = \alpha_\varphi\varphi[t-1] + \angle\left\{\sum\nolimits_{d=1}^{L-1} y_{filt}[d,t]\times\overline{y}_{filt}[d,t-1]\right\} \qquad (4)$$

wherein, $\varphi[t]$ is an unwrapped phase for the $t^{th}$ instance. $\alpha_\varphi$, is a high pass factor. $\varphi[t-1]$ is the unwrapped phase for the $[t-1]^{th}$ instance. L is the number of fast time samples. $y_{filt}[d,$ t] is the corresponding element of the range-time matrix and $\overline{y}_{filt}$[d, t-1] is the conjugate of y[d, t-1].

Further, a second order derivative of the obtained low pass filtered unwrapped phase is estimated, wherein the second order derivative denotes curvature in the body part.

At the next step 308 of the method 300, the one or more hardware processors 108 are configured by the programmed instructions to estimate one or more along-track bins associated with the predefined region of the body part where one or more orthopedic implants are comprised, wherein the one or more along-track bins provide a predefined location of the topography information of the body part in a SAR image.

In the SAR imaging, the knowledge of the target's center location plays a significant role in generating focused images. Given a fixed wavelength and fixed along-track antenna length, the synthetic aperture length ($L_{sa}$) $L_{sa}$=$\lambda R_0$/ $D_{at}$ is dependent upon the target range. Herein, $D_{at}$ is the along track antenna wavelength, $\lambda$ is the transmitting wavelength, and $R_0$ is the target range. For satellite-borne SAR, the phase correction considers a single focus point corresponding to the center of radar footprint.

Furthermore, the range of this focus point is large (usually hundreds of kilometers) as compared to the bin spacing. For short range applications, the range and the bin spacing becomes comparable. In the present disclosure, an auto-focus technique is implemented by the system and method of the present disclosure has been used to estimate the near and far swath from multiple fast-time profiles in the SAR complex data. The pulse-width at the mid-reference level of the fast-time waveform has been used to approximate the spread function of the object/region. The auto-focus technique splits the spread-function into multiple windows which are then used as focus points. These are used to compute respective $L_{sa}$ values which are further utilized in the Range Doppler Algorithm (RDA) to generate focused images of the target scene.

At the next step 310 of the method 300, the one or more hardware processors 108 are configured by the programmed instructions to obtain an SAR amplitude image by taking absolute value of the SAR complex data.

At the next step 312 of the method 300, the one or more hardware processors 108 are configured by the programmed instructions to localize the one or more orthopedic implants in the body part of the subject using the obtained SAR amplitude image and the one or more along-track bins. The mmWave SAR and consecutive autofocusing SAR imaging are suitable for superficial tissue and subsequent continuous implant monitoring due to their smaller form-factor and faster processing coupled with focused dielectric lens.

Herein, the SAR amplitude image is obtained by performing a range compression on the SAR complex data to obtain a range-compressed matrix. Further, an azimuth Fast Fourier Transform (FFT) is performed on the range-compressed matrix to obtain a range doppler matrix. An azimuth compression is performed by multiplying the range doppler matrix with FFT of a time-domain azimuth reference function to obtain a matched filter output. Finally, an azimuth Inverse Fast Fourier Transform (IFFT) is performed to transform the matched filter output into a time domain to form a complex image matrix and to obtain the SAR amplitude image by taking an absolute value of the complex image matrix.

Additionally, the auto focus technique enables to efficiently image non-homogeneous human limb. These been rigorously and successfully tested with bone phantom implants and a human subject with 2 screws superficially inserted in tibia. 1 cm and 2 cm metallic point scatterers were detected perfectly, whereas for the 0.5 cm scatterer there is an error of 0.18 cm, due to the limitation of the radar hardware. A disproportionate spread in the intensity for 0.5 cm point scatterer, while the same is not observed for 1 cm and 2 cm point scatterer. This may be limited by hardware range resolution limitation. The diameter of the point scatter is observed to match the dimension of the highest intensity inner region of the range-cross range plots for 1 cm and 2 cm diameter point object scatterer.

Figure 4A:
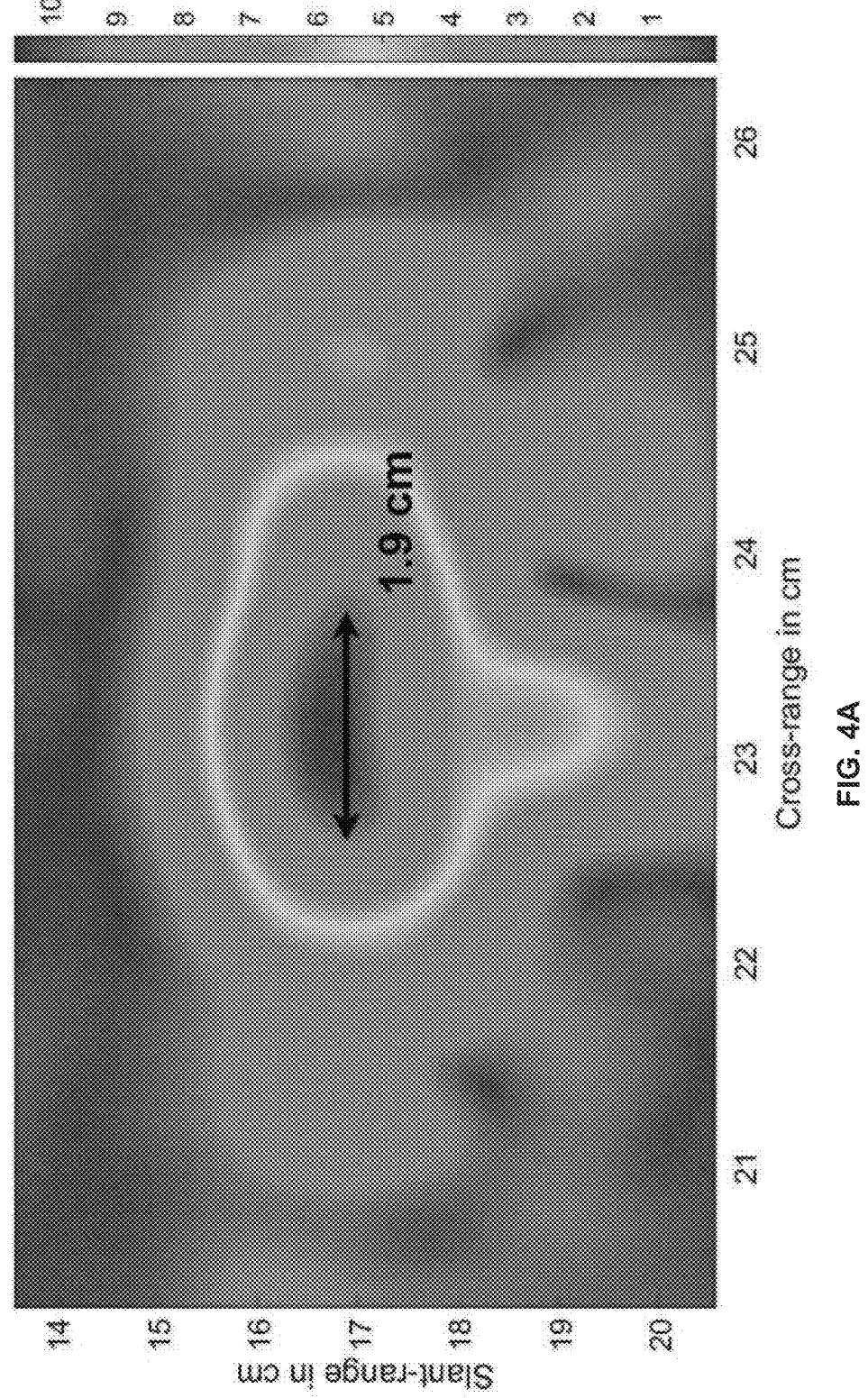
FIGS. 4A, 4B, and 4C (collectively FIG. 4) are schematic diagrams to illustrate a range azimuth plots for point scatterers, in accordance with some embodiments of the present disclosure.
Figure 4B:
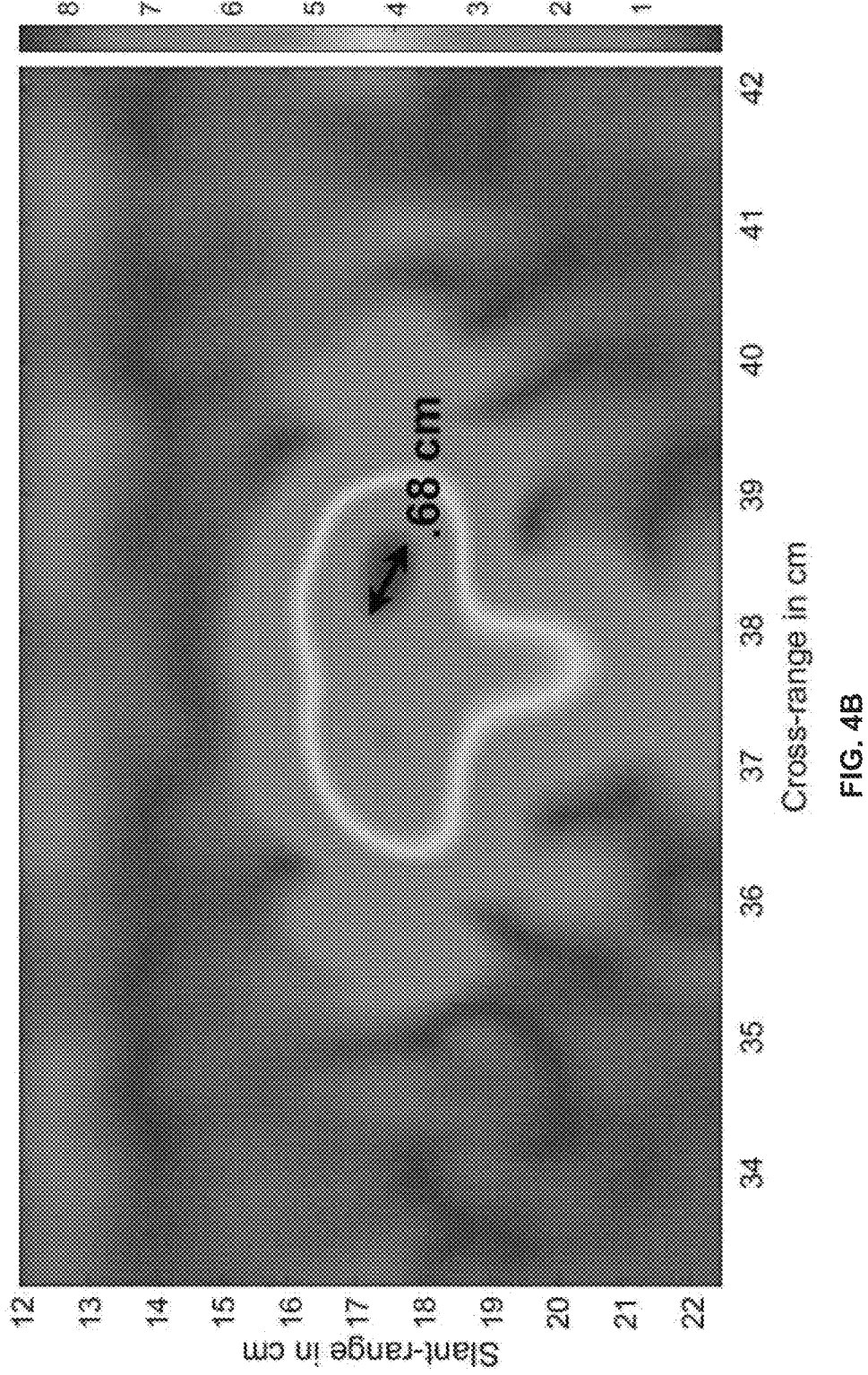
Figure 4C:
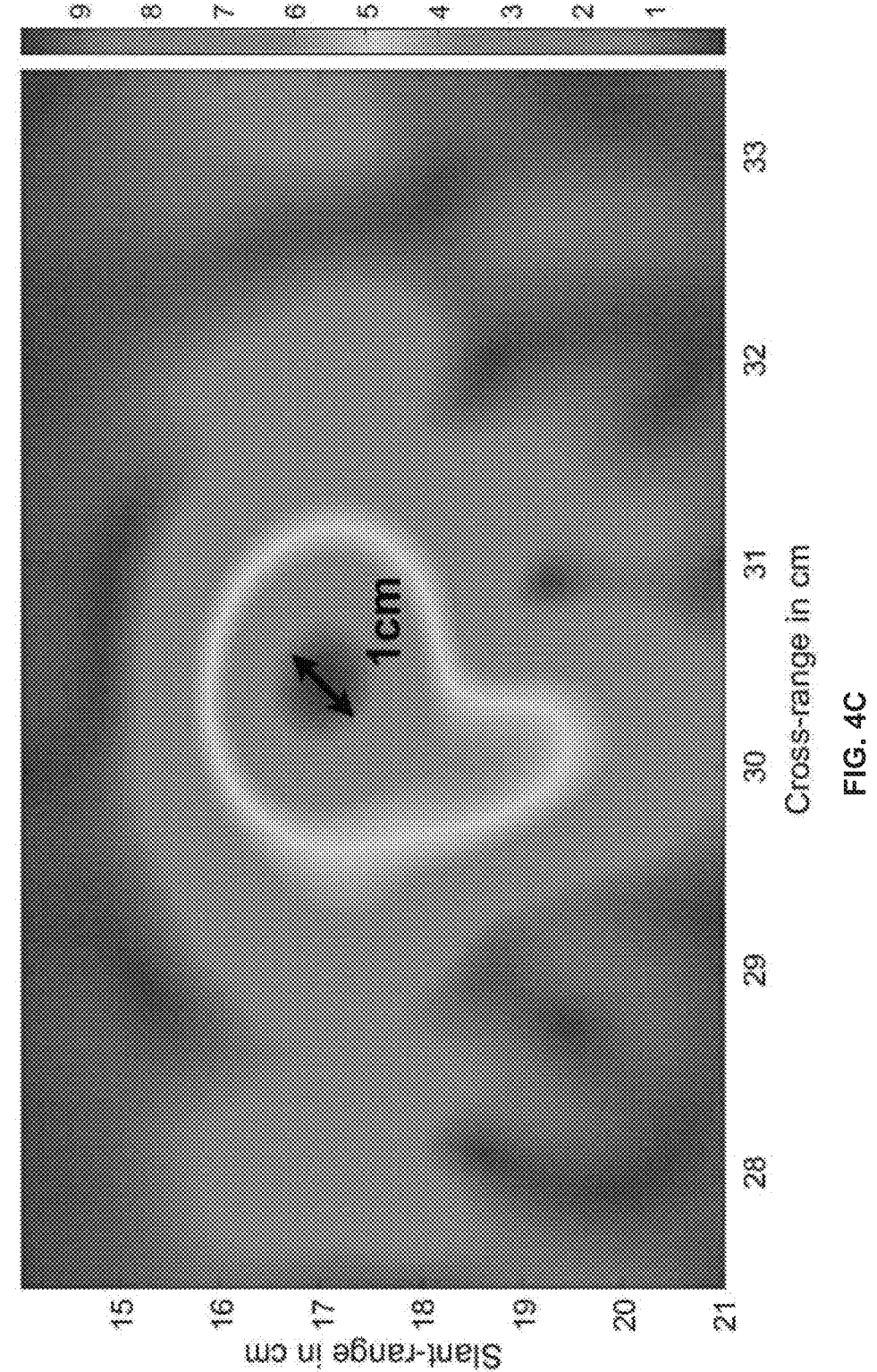

It has also been experimentally observed as shown in FIGS. 4A through 4C that in cross range direction, only when two objects are placed more than 1.5 cm apart, these can distinguish as separate entities. Out of three different types of metallic inserts in sawbones phantom, two were detected with 100% accuracy and third type with 93.5% accuracy in terms of implant dimension and location. In the case of two screws on human tibia, both were detected accurately, while their inter-spacing distance accuracy was 76.2%.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address the need of a technique for superficial tissue imaging to monitor metallic implants. Embodiments herein provide method and system for superficial tissue imaging to monitor metallic implants using the mmWave SAR. The mmWave SAR and consecutive autofocusing SAR imaging are suitable for superficial tissue and subsequent continuous implant monitoring due to their smaller form-factor and faster processing coupled with focused dielectric lens. Additionally, a limb topography is approximated for localization of implant region on interest (ROI) in the SAR amplitude image.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software modules located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

What is claimed is:

1. A processor-implemented method comprising:
scanning, via a millimeter-wave (mmWave) radar, a body part of a subject comprising one or more orthopedic implants;
obtaining, via one or more hardware processors, an uncompressed synthetic aperture radar (SAR) complex data from the mmWave radar, wherein the uncompressed SAR complex data comprises a real part and an imaginary part;
extracting, via the one or more hardware processors, a topography information of a predefined region of the body part from the SAR complex data;
estimating, via the one or more hardware processors, one or more along-track bins associated with the predefined region of the body part where one or more orthopedic implants are comprised, wherein the one or more along-track bins provide a predefined location of the topography information of the body part in a SAR image;

obtaining, via the one or more hardware processors, an SAR amplitude image by taking absolute value of the SAR complex data; and
localizing, via the one or more hardware processors, the one or more orthopedic implants in the body part of the subject using the obtained SAR amplitude image and the one or more along-track bins.

2. The processor-implemented method of claim 1, wherein obtaining the SAR amplitude image comprises:
performing a range compression on the SAR complex data to obtain a range-compressed matrix;
performing an azimuth Fast Fourier Transform (FFT) on the range-compressed matrix to obtain a range doppler matrix;
performing an azimuth compression by multiplying the range doppler matrix with FFT of a time-domain azimuth reference function to obtain a matched filter output;
performing an azimuth Inverse Fast Fourier Transform (IFFT) to transform the matched filter output into a time domain to form a complex image matrix; and
obtaining the SAR amplitude image by taking an absolute value of the complex image matrix.

3. The processor-implemented method of claim 1, wherein the topography information of the body part is extracted by:
obtaining in-phase and quadrature phase components of the SAR complex data;
performing an arctan operation on the SAR complex data to obtain a phase of the SAR complex data;
unwrapping the phase of SAR complex data by using the expression:

$$\varphi[t] = \alpha_\varphi \varphi[t-1] + L\left\{\sum_{d=1}^{L-1} y_{filt}[d,t] \times \bar{y}_{filt}[d,t-1]\right\}$$

wherein, $\varphi[t]$ is an unwrapped phase for the tth instance, $\alpha_\varphi$ is a high pass factor, $\varphi[t-1]$ is the unwrapped phase for the $[t-1]^{th}$ instance, L is the number of fast time samples, $y_{filt}[d,t]$ is the corresponding element of the range-time matrix and $\bar{y}_{filt}[d,t-1]$ is the conjugate of $y[d,t-1]$;
applying a low pass filter on the unwrapped phase of the SAR complex data to obtain low pass filtered unwrapped phase; and
estimating a second order derivative of the obtained low pass filtered unwrapped phase, wherein the second order derivative denotes curvature in the body part.

4. The processor-implemented method of claim 1, wherein an auto-focus technique is used to estimate a near and far swath from one or more fast-time profiles in the SAR complex data.

5. A system comprising:
a millimeter-wave (mmWave) to scan a body part of a subject comprising one or more orthopedic implants;
a memory in communication with the one or more hardware processors, wherein the one or more hardware processors are configured to execute programmed instructions stored in the memory to:
obtain an uncompressed synthetic aperture radar (SAR) complex data from the mmWave radar, wherein the uncompressed SAR complex data comprises a real part and an imaginary part;
extract a topography information of a predefined region of the body part from the SAR complex data;

estimate one or more along-track bins associated with the predefined region of the body part where one or more orthopedic implants are comprised, wherein the one or more along-track bins provide a predefined location of the topography information of the body part in a SAR image;

obtain an SAR amplitude image by taking absolute value of the SAR complex data; and localize the one or more orthopedic implants in the body part of the subject using the obtained SAR amplitude image and the one or more along-track bins.

6. The system of claim 5, wherein obtaining the SAR amplitude image by:

performing a range compression on the SAR complex data to obtain a range-compressed matrix;

performing an azimuth Fast Fourier Transform (FFT) on the range-compressed matrix to obtain a range doppler matrix;

performing an azimuth compression by multiplying the range doppler matrix with the FFT of a time-domain azimuth reference function to get the matched filter output;

performing an azimuth Inverse Fast Fourier Transform (IFFT) to transform matched filter output into a time domain to form a complex image matrix; and obtaining the SAR amplitude image by taking absolute value of complex the image matrix.

7. The system of claim 5, wherein the topography information of the body part is extracted by:

obtaining in-phase and quadrature phase components of the SAR complex data;

performing arctan operation on the SAR complex data to obtain a phase of the SAR complex data;

unwrapping the phase of SAR complex data by using the expression $$\varphi[t] = \alpha_\varphi \varphi[t-1] + \angle\left\{\sum_{d=1}^{L-1} y_{filt}[d, t] \times \overline{y}_{filt}[d, t-1]\right\}$$

wherein, $\varphi[t]$ is an unwrapped phase for the tth instance, $\alpha_\varphi$ is a high pass factor, $\varphi[t-1]$ is the unwrapped phase for the $[t-1]^{th}$ instance, L is the number of fast time samples, $y_{filt}[d, t]$ is the corresponding element of the range-time matrix and $\overline{y}_{filt}[d, t-1]$ is the conjugate of $y[d, t-1]$;

applying a low pass filter on the unwrapped phase of the SAR complex data to obtain low pass filtered unwrapped phase; and estimating a second order derivative of the obtained low pass filtered unwrapped phase, wherein the second order derivative denotes curvature in the body part.

8. The system of claim 5, wherein an auto-focus technique is used to estimate a near and far swath from one or more fast-time profiles in the raw data.

9. One or more non-transitory machine-readable information storage mediums comprising one or more instructions which when executed by one or more hardware processors cause:

scanning, via a millimeter-wave (mmWave) radar, a body part of a subject comprising one or more orthopedic implants;

obtaining an uncompressed synthetic aperture radar (SAR) complex data from the mmWave radar, wherein the uncompressed SAR complex data comprises a real part and an imaginary part;

extracting a topography information of a predefined region of the body part from the SAR complex data;

estimating one or more along-track bins associated with the predefined region of the body part where one or more orthopedic implants are comprised, wherein the one or more along-track bins provide a predefined location of the topography information of the body part in a SAR image;

obtaining an SAR amplitude image by taking absolute value of the SAR complex data; and localizing the one or more orthopedic implants in the body part of the subject using the obtained SAR amplitude image and the one or more along-track bins.

10. The one or more non-transitory machine-readable information storage mediums of claim 9, wherein obtaining the SAR amplitude image comprises:

performing a range compression on the SAR complex data to obtain a range-compressed matrix;

performing an azimuth Fast Fourier Transform (FFT) on the range-compressed matrix to obtain a range doppler matrix;

performing an azimuth compression by multiplying the range doppler matrix with FFT of a time-domain azimuth reference function to obtain a matched filter output;

performing an azimuth Inverse Fast Fourier Transform (IFFT) to transform the matched filter output into a time domain to form a complex image matrix; and obtaining the SAR amplitude image by taking an absolute value of the complex image matrix.

11. The one or more non-transitory machine-readable information storage mediums of claim 9, wherein the topography information of the body part is extracted by:

obtaining in-phase and quadrature phase components of the SAR complex data;

performing an arctan operation on the SAR complex data to obtain a phase of the SAR complex data;

unwrapping the phase of SAR complex data by using the expression:

$$\varphi[t] = \alpha_\varphi \varphi[t-1] + \angle\left\{\sum_{d=1}^{L-1} y_{filt}[d, t] \times \overline{y}_{filt}[d, t-1]\right\}$$

wherein, $\varphi[t]$ is an unwrapped phase for the $t^{th}$ instance, $\alpha_\varphi$ is a high pass factor, $\varphi[t-1]$ is the unwrapped phase for the $[t-1]^{th}$ instance, L is the number of fast time samples, $y_{filt}[d, t]$ is the corresponding element of the range-time matrix and $\overline{y}_{filt}[d, t-1]$ is the conjugate of $y[d, t-1]$;

applying a low pass filter on the unwrapped phase of the SAR complex data to obtain low pass filtered unwrapped phase; and estimating a second order derivative of the obtained low pass filtered unwrapped phase, wherein the second order derivative denotes curvature in the body part.

12. The one or more non-transitory machine-readable information storage mediums of claim 9, wherein an auto-focus technique is used to estimate a near and far swath from one or more fast-time profiles in the SAR complex data.

* * * * *